(12) United States Patent
Rao et al.

(10) Patent No.: US 6,489,514 B1
(45) Date of Patent: Dec. 3, 2002

(54) (-)-SECOISOLARICIRESINOL AS AN ANTIOXIDANT OBTAINED FROM A NEW NATURAL SOURCE NAMELY *STEREOSPERMUM PERSONATUM*

(75) Inventors: Janaswamy Madhusudana Rao, Andhra Pradesh (IN); Ashok Kumar Tiwari, Andhra Pradesh (IN); Upparapalli Sampath Kumar, Andhra Pradesh (IN); Jhillu Singh Yadav, Andhra Pradesh (IN); Kondapuram Vijaya Raghavan, Andhra Pradesh (IN)

(73) Assignee: Council of Scientific and Industrial Research, New Delphi (IN)

( * ) Notice: Subject to any disclaimer, the term of this patent is extended or adjusted under 35 U.S.C. 154(b) by 0 days.

(21) Appl. No.: 09/917,607

(22) Filed: Jul. 27, 2001

(51) Int. Cl.7 ............................................. C07C 43/253
(52) U.S. Cl. ....................... 568/644; 568/652
(58) Field of Search ................. 568/644, 652; 514/721, 773, 777, 789, 22; 424/451, 464, 489; 530/500

(56) References Cited

U.S. PATENT DOCUMENTS 4,473,620 A * 9/1984 Wu et al. .................... 252/404
5,837,256 A * 11/1998 Clark et al. .................... 514/25
6,261,565 B1 * 7/2001 Empie et al. ................ 424/725

FOREIGN PATENT DOCUMENTS

CA      2312164      * 12/2000      .......... A61K/31/70

OTHER PUBLICATIONS

Obermeyer et al., Chemical Studies of Phytoestrogens and Related Compunds in Dietry Supplements: Flax and Chaparral, No month Provided 1995, Society for Experimental Biology and Medicine, vol. 208, pp. 6–12.*

* cited by examiner

*Primary Examiner*—Rosalynd Keys
(74) *Attorney, Agent, or Firm*—Merchant & Gould P.C.

(57) ABSTRACT

This invention relates to a pharmaceutical composition comprising an effective amount of (−)-Secoisolariciresinol together with or associated with an additive useful as an antioxidant; a process for isolating the (−)-Secoisolariciresinol from the plant *Stereospermum Personatum* and also relates to use of the active fraction (−)-Secoisolariciresinol as an antioxidant or free radical scavenger.

3 Claims, 1 Drawing Sheet

(−)-Secoisolariciresinol

Figure 1:
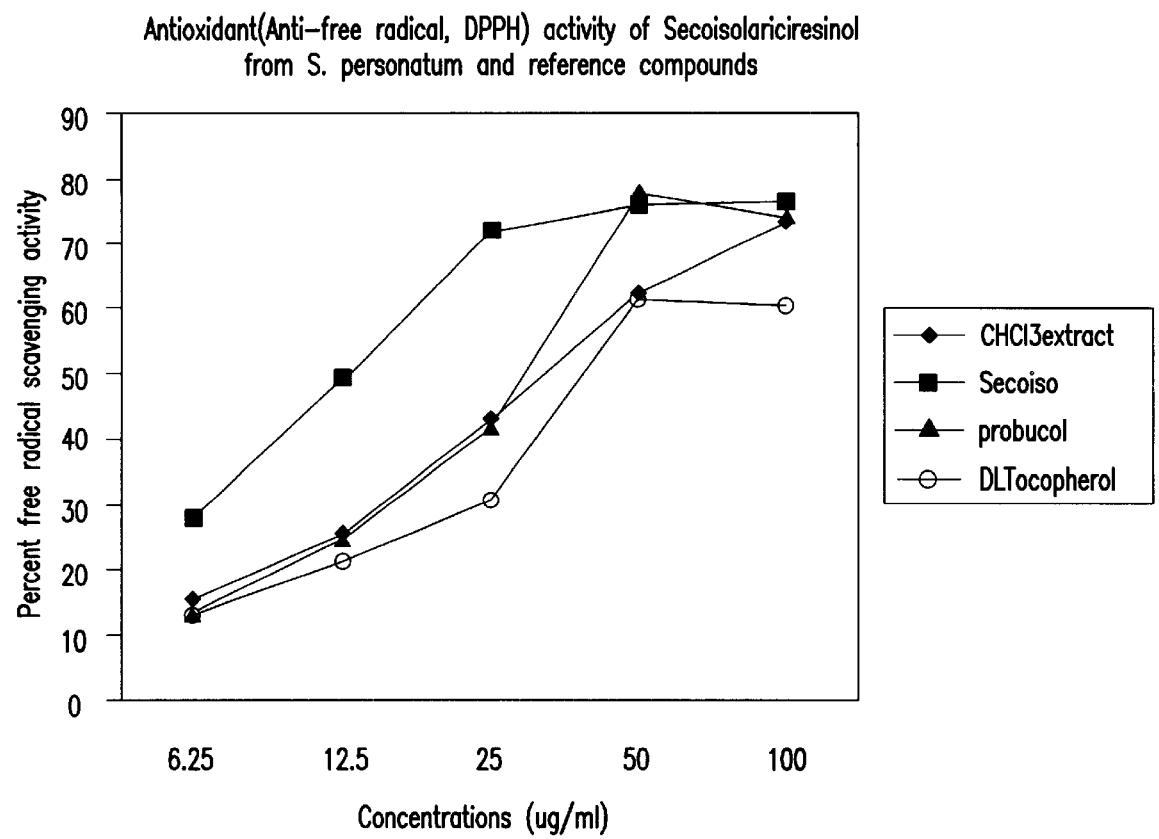

(-)-SECOISOLARICIRESINOL AS AN ANTIOXIDANT OBTAINED FROM A NEW NATURAL SOURCE NAMELY *STEREOSPERMUM PERSONATUM*

FIELD OF THE INVENTION

This invention relates to the isolation of compound namely (-)-Secoisolariciresinol from a new plant source *Stereospermum personatum*. The compound (-)-Secoisolariciresinol {2,3Bis-[4-hydroxy-3-(methoxyphenyl) methyl]-1,4-butanediol} is isolated from new source in good yield.

It is proved to be useful and better antioxidant molecule than the presently used medicinally important lipophilic antioxidants Prubucol and α-Tocopherol. It may have better therapeutic potential in inflammatory disease conditions, atherosclerosis, diabetic complications, cancer, hepatotoxicity and variety of disease conditions mediated through or fostered by oxidative stress and/or overt oxidative burden due to increased generation or under scavenging of free radicals.

BACKGROUND AND PRIOR ART REFERENCES

There is a considerable amount of epidemiological evidence indicating association between diet rich in fruits and vegetables and a decreased risk of cardiovascular disease and certain forms of cancer. It is generally assumed that the active principles contributing to these protective effects are nothing but primarily, the antioxidant phytochemicals.

Research in the past decades have accumulated enough evidence to show the beneficial effect of free-radical scavengers/antioxidants as antimutagenic, anti-inflammatory, antiamerosclerotic, antidiabetic, antihepatotoxic, antiageing and in a variety of neurological disorders. The search for new antioxidant principles is becoming therefore, essential to improve the pharmacological treatment of pathological conditions such as cataract, rheumatic diseases, atherosclerosis, Alzheimer's disease and other neurodegenarative conditions.

The pharmacological approaches therefore have focused on the search of potential resources rich in with antioxidant principles. The medicinal importance of plants bearing rich proportion of antioxidant principles is therefore becoming hot item.

*Stereospermum personatum* is a medicinal plant used in traditional Indian System of Medicine and is widely advocated in the preparations for diuretic, lithontriptic, expectorant, cardiotonic, aphrodisiac, appetizer, anti-inflammatory, antibacterial. dyspepsia, diarrhea, renal and vesical calculi, cough, asthma, hyperdipsia, haemorrhoids and hyperacidity disease conditions (Indian Medicinal Plants, Vol 5 p 192). It is further reported to possess antibacterial, antifungal, hypoglycemic activity, and against p388 lymphocytic leukemic cells (Ind. Jour, of Exp. Biol., 1971,9, 100). Hence, it becomes pertinent to look for the molecules possessing such important biological properties. In this connection, the phytochemical investigation of *Stereospermum personatum* has been taken up. The applicants have isolated (-)-Secoisolariciresinol in good yields. (-)-Secoisolariciresinol is known to possess several activities, which are shown in Table 1.

TABLE 1

| Compound | Activity | Reference |
| --- | --- | --- |
| (-)-Secoisolariciresinol | 1. Antitumor agent | Japanese Pat. No. JP0131J17 |
| | 2. Cardiotonic | Japanese Pat No. JP02,101,011 |
| | 3. Binding to SHBG | Z. Naturforsch, C. Biosc. 997,52,834–843 |

OBJECTS OF THE INVENTION

The main object of the invention is to provide novel composition containing (-)-Secoisolariciresinol in combination with or associated with additives and useful as an antioxidant.

Another object is to provide a new source for obtaining (-)-Secoisolariciresinol in significant yields.

Yet another object of the invention is to provide a process for producing (-)-Secoisolariciresinol from a plant namely *Stereospermum personatum*.

One more object of the invention relates to use of (-)-Secoisolariciresinol as an antioxidant.

SUMMARY OF INVENTION

In accordance with this invention, it has been found that (-)-Secoisolariciresinol is isolated from a new plant source, *Stereospermum Personatum* in significant yield. Also, it has been found that (-)-Secoisolariciresinol show antioxidant property.

DETAILED DESCRIPTION OF THE INVENTION

Accordingly, the invention provides a novel composition containing (-)-Secoisolariciresinol and useful as antioxidant. The invention further provides a method for the isolation of (-)-Secoisolariciresinol from a new source namely *Stereospermum Personatum*.

Antioxidant compounds recently have attracted the attention due to their broad spectrum of activities in disorders of multiple origin viz., coronary heart disease, cancer, diabetes, rheumatic disorders and inflammatory conditions where free radicals play important role. Much attention is being directed now to harness and harvest the antioxidant compounds from natural resources.

The compound (-)-Secoisolariciresinol is used in pure form. Hence, the usage may be more advantageous than a mixture of compounds having similar properties, which are in current use. It is also important to note that the process of isolation of (-)-Secoisolariciresinol is highly economical.

Accordingly, the present invention provides a useful source, *Stereospermum Personatum*, comprising antioxidant principle of which (-)-Secoisolariciresinol is isolated as pure and potent antioxidant molecule. (-)-Secoisolariciresinol has been compared with existing pharmacologically/therapeutically accepted antioxidant Probucol and alpha-tocopherol.

It is found that (-)-Secoisolariciresinol is better than the above mentioned reference drugs and hence may be used with pharmaceutically/therapeutically acceptable additives.

In an embodiment of the present invention, (-)-Secoisolariciresinol may be effective in much less amount than the reference drugs mentioned above.

In an embodiment of the present invention relates to a composition useful as antioxidant, said composition comprising an effective amount of (–)-Secoisolariciresinol in combination with or associated with a pharmaceutically acceptable additives.

In another embodiment of the invention, the pharmaceutically acceptable additive is selected in such a manner that it does not affect or interfere with the efficacy of (–)-Secoisolariciresinol.

In still another embodiment of the invention, the additive is selected from nutrients such as carbohydrates, sugar, proteins, fats and pharmaceutically acceptable carrier.

In yet another embodiment of the invention, the amount of (–)-Secoisolariciresinol administered is in the range between 200 mg to 250mg per dose at least twice a day.

In an embodiment of the present invention, the ratio of (–)-Secoisolariciresinol to the additive is in the range between 0.1:10 to 3:10, preferably 0.4:10 to 2:10.

In yet another embodiment of the invention, the composition is administered through oral route in the form of tablets, capsules, syrup or powder.

One embodiment of the invention relates to a process for isolation of (–)-Secoisolariciresinol from the plant *Stereospermum personatum* said process comprising the steps of:

a) extracting the dried wood powder of *Stereospermum personatum* with hexane;

b) further extracting the residue from step (a) with chloroform;

c) concentrating the chloroform solution from step (b) under vacuum;

d) absorbing the dark brown extract on a silicaget (60–120 mesh) and loaded on silicagel (60–120 mesh) column (4 cm diameter to height of 100 cm);

e) eluting the column with chloroform methanol gradient, and f) collecting the eluted fraction with 3% methanol in chloroform and concentrating the fraction to obtain pure (–)-Secoisolariciresinol.

In another embodiment of the present invention, the solvents used are selected from hexane, chloroform and methanol.

In another embodiment of the present invention, the yield of (–)-Secoisolariciresinol obtained is about 0.03% of the plant dried material.

One more embodiment relates to use of (–)-Secoisolariciresinol as an antioxidant or free-radical scavenger animals and human beings.

In yet another embodiment relates to use of (–)-Secoisolariciresinol for the manufacturing of a composition useful as antioxidant.

In yet another embodiment of the present invention, (–)-Secoisolariciresinol is administered orally.

Yet another embodiment of the invention relates to a method for the treatment of free radical scavenging, comprising the steps of administering an effective amount of (–)-Secoisolariciresinol to a subject in need thereof, preferably, (–)-Secoisolariciresinol is administered in the range of 200 mg–250 mg/dose, at least twice a day.

*Stereospermum personatum* hence is a new source for (–)-Secoisolariciresinol and its presence in this plant in good yields makes this invention more important. A comparison of yield (–)-Secoisolariciresinol from different plants is given in Table. 2

TABLE 2

| Name of the plant | % yield of (–)-Secoisolariciresinol | Reference |
| --- | --- | --- |
| *Carissa edulis* | 0.0004 | Phytochemistry, 1983,22,749 |
| *Juniperus chinensis* | 0.00245 | Phytochemistry, 1992,31,3659 |
| *Stereospermum personatum* | 0.03 | Present invention |

The present invention embodies isolation of (–)-Secoisolariciresinol, as antioxidant principle from a new plant source and identify its free radical scavenging property compared with medicinally important antioxidant drug molecules.

BRIEF DESCRIPTION OF THE ACCOMPANYING DRAWING

Figure 2:
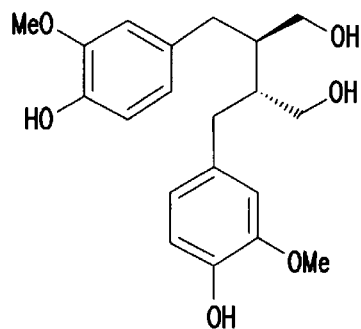

FIG. 1 shows antioxidant (Anti-free radical, DPPH) activity of (–)-Secoisolariciresinol from *Stereospermum personatum* and reference compounds FIG. 2 shows the structural formula of (–)-Secoisolariciresinol The invention is further described in the following examples that are given by the way of illustration and therefore should not be construed to limit the invention in any manner.

EXAMPLE 1

Experimental Protocol

A process for the isolation of above lignans.

The dried wood powder of *Stereospermum personatum* (3 Kg) was loaded on a Soxhlet apparatus. The powder was first extracted with hexane. The residue from the extraction of hexane was further extracted with chloroform. The chloroform solution was concentrated under vacuum. The dark brown extract (22 g) was adsorbed on silica gel (60–120 mesh) and loaded on silica gel (60–120 mesh) column. (4 cm dia to a height of 100 cms).

The column is subjected to elution with chloroform methanol gradient. The chloroform-methanol gradient is so selected to obtain specific fraction and thereby the desired compound. In the present case, the fractions eluted at 3% methanol in chloroform are collected separately and concentrated.

The above fractions are subjected to further purification using silica gel column (>200 mesh, 2.5 cm dia and 50 cm length) using chloroform methanol gradient. The eluent at 3% methanol in chloroform gave pure (–)-Secoisolariciresinol (0.9 g). The spectrochemical data of (–)-Secoisolariciresinol are given below:

(–)-Secoisolariciresinol

1. Molecular formula: $C_{20}H_{26}O_6$
2. $^1$HNMR: δ 1.82(2H, m), 2.6(2H, dd), 2.7(2H, dd), 3.55 (2H, dd), 3.80(6H, s), 3.85(2H, d), 5.4 (Ar—OH, brs), 6.55 (2H, s), 6.6(2H, d), 6.8(2H, d).
3. $^{13}$CNMR: δ 34.02(C-7), 42.55(C-8), 55.51 (2×OCH$_3$) 60.32(C-9), 113.07(C-2), 115.09(C-5), 121.17(C-6), 132.26(C-1), 144.31l(C-4), 147.26(C-3).
4. MS: 362(M$^+$)
5. IR: 3422 cm$^{-1}$ (OH)

EXAMPLE 2

In Vitro Evaluation of Free Radical Scavenging Antioxidant Potency

Antioxidant activity of the compounds was tested for its capacity/potency to scavenge most widely used free radical, 1,1-diphenyl-2-picryl hyrazyl radical (DPPH). The well-accepted and tested antioxidants namely probucol and α-tocopherol were taken as reference compounds. 1mg/ml DMSO concentration of the compounds were prepared and subsequently, diluted to lower concentrations with DMSO. 200 μl of test compounds were reconstituted to 1 ml in tris-HCl buffer (pH 7.4). Equal volume of 500 μM of DPPH radical dissolved in ethanol was reacted with this. After incubation for 45 minutes in dark, the absorbency at 517 nm was recorder. Percent radical scavenging activity was calculated accordingly. All the readings were taken in triplicate. Result (FIG. 1 and Table 3) shows that compound under consideration possess potent antioxidant/free- radical scavenging property.

TABLE 3

50% Radical scavenging concentration of compounds.

| Antioxidant | Concentration (μg/ml) |
|---|---|
| CHCl$_3$ Extract | 40.09 |
| (−)-Secoisolariciresinol | 13.72 |
| Probucol | 28.71 |
| DL α- Tocopherol | 47.80 |

What is claimed is:

1. A process for isolation of (−)-Secoisolariciresinol from the plant *Stereospermum personatum*, said process comprising the steps of:
   a) extracting dried wood powder of *Stereospermum personatum* with hexane;
   b) extracting the residue from step (a) with chloroform;
   c) concentrating the chloroform solution from step (b) under vacuum;
   d) absorbing the dark brown extract on a silicagel (60–120mesh) and loaded on silicagel (60–120 mesh) column (4 cm dia to height of 100 cm);
   e) eluting the column with chloroform methanol gradient, and
   f) collecting the eluted fraction with 3% methanol in chloroform and concentrating the fraction to obtain pure (−)-Secoisolariciresinol.

2. A process as claimed in claim 1, wherein the yield of (−)-Secoisolariciresinol is about 0.03% of the plant dried material.

3. A process for obtaining (−)-Secoisolariciresinol comprising performing an extraction on dried wood powder of *Stereospermum personatum* and recovering (−)-Secoisolariciresinol from an extracted fraction.

* * * * *